United States Patent [19]

Kanno et al.

[11] Patent Number: 4,458,063
[45] Date of Patent: Jul. 3, 1984

[54] 2-METHYL-1,3-PROPYLENE GLYCOL MONO- OR DI-ALKYLENE OXIDE ETHER

[75] Inventors: Tatsuya Kanno; Yuzo Toga, both of Himeji, Japan

[73] Assignee: Daicel Chemical Industries, Ltd., Osaka, Japan

[21] Appl. No.: 485,687

[22] Filed: Apr. 18, 1983

[30] Foreign Application Priority Data

Apr. 22, 1982 [JP] Japan ................................. 57-67885
Apr. 22, 1982 [JP] Japan ................................. 57-67886
Apr. 22, 1982 [JP] Japan ................................. 57-67887

[51] Int. Cl.³ .............................................. C08G 59/22
[52] U.S. Cl. ..................................... 528/418; 430/280; 528/421; 549/555
[58] Field of Search ............... 528/418, 421; 549/555; 430/280

[56] References Cited

U.S. PATENT DOCUMENTS 2,538,072  1/1951  Zech ............................... 549/555 X
4,216,288  8/1980  Crivello ........................... 528/90 X
4,346,163  8/1982  Takeyama et al. ................. 430/280

Primary Examiner—Earl A. Nielsen
Attorney, Agent, or Firm—Flynn, Thiel, Boutell & Tanis

[57] ABSTRACT

There is disclosed a novel 2-methyl-1,3-propylene glycol mono- or di-alkylene oxide ether having the formulae (I) or (II):

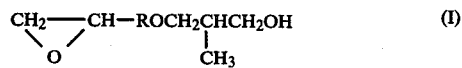

(I)

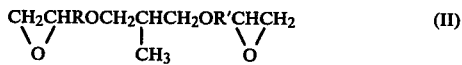

(II)

in which R and R' are linear or branched alkylene groups with $C_1$–$C_3$. The di-alkylene oxide ether is useful as an active ingredient for a photocurable composition.

2 Claims, No Drawings

2-METHYL-1,3-PROPYLENE GLYCOL MONO- OR DI-ALKYLENE OXIDE ETHER

This invention deals with a mono- or di-alkylene oxide ether of 2-methyl-1,3-propylene glycol. The compound is useful as coating, adhesive, binder, and the like. Especially the dialkylene oxide is useful as an active ingredient for a photocurable composition.

This invention further concerns a curable composition whose effective ingredient is a 2-methyl-1,3-propylene glycol dialkylene oxide ether. More specifically, this invention deals with a curable composition with a superior adherence to the base plate of which only the exposed portion is converted to a material which is insoluble or slightly soluble in the developing solution upon exposure to activating rays.

In general, glycol monoalkylene oxide ether compounds are synthesized by the reaction of halogenated alkylene oxides such as epihalohydrin and glycols.

The glycols mentioned above which had been used for this purpose are ethylene glycol, diethylene glycol, triethylene glycol, tetraethylene glycol, propylene glycol, 1,3-butylene glycol, 1,4-butylene glycol, neopentylene glycol, 1,6-hexamethylene glycol, and bisphenol A. The glycol monoalkylene oxide ether compounds obtained from these glycols have an epoxide group which can be cross-linked and an active hydroxyl group in each molecule. The glycol monoalkylene oxide ether compounds can be used in an extremely wide variety of applications, including ultraviolet ray or heat curing paints, adhesives, non-woven clothbinders, paper processing, modifying agents, for copolymers, ion-exchange resins, and dental material, and as crosslinking agents, starting materials, intermediates, and reactive diluents. In order to obtain the glycol monoalkylene oxide ether most suitable for each application, the glycol for the synthesis had to be very carefully selected.

In the past, liquid compounds which had relatively high boiling points and which cured well have been selected as curable compounds, since they are easy to handle at normal pressure and temperature and their ignition points and toxicities are very low. The polyepoxy compounds which normally contain more than 2 epoxy groups in each molecule have often been used as the compounds which satisfied the conditions described above, and curable compositions containing such polyepoxy compounds have been researched for a long time. There are many types of polyepoxy compounds. For example, the most representative types are the epoxy ether of polyalkylene glycol which is linked by ether linkages and the epoxy ethers of polyalcohols. Of these, the epoxy ethers of polyalcohols are mostly high-boiling liquids and are curable themselves upon exposure to the activating rays. They are widely used in curable compositions for ultraviolet-ray or heat curing paints and ultraviolet-ray curing inks, since they form excellent cured films when dissolved in other polymeric substances (henceforth referred to as filling polymeric compounds) or mixed with the acrylate or methacrylate ester of polyalcohols containing terminal ethylenic unsaturated bonds which increase the sensitivity.

The inventors have worked hard to expand the range of selection and discovered that 2-methyl-1,3-propylene glycol mono- or di-alkylene oxide ethers synthesized using 2-methyl-1,3-propylene glycol as the glycol were totally novel compounds. This invention was completed based on this discovery.

In other words, this invention presents novel glycol mono- or di-alkylene oxide ether compounds represented by the general formulae (I) and (II), respectively

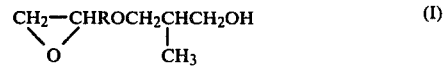

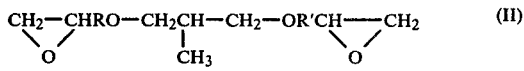

(in which R and R' are a linear or branched alkylene group with $C_1$–$C_3$).

The inventors have further found that the curable compound containing the said compound as the effective ingredient had a fast curing speed and formed an image with excellent adhesion to the base plate when used in photoresists, etc. This invention was completed based on this discovery.

2-Methyl-1,3-propylene glycol, which is the glycol component in the 2-methyl-1,3-propylene glycol monoalkylene oxide ether compounds of this invention, can be produced industrially by the oxidation reaction of isobutene or by the oxo reaction of allyl alcohol. 2-Methyl-1,3-propylene glycol is an unusual glycol, extremely high in chemical reactivity, since its chemical structure includes one methyl group on the carbon atom in the 2 position, and as a result, the main molecular chain is asymmetric; in addition, both terminal hydroxyl groups are primary hydroxyl groups.

2-Methyl-1,3-propylene glycol monoalkylene oxide ethers of this invention can be synthesized by the reactions of halogenated alkylene oxides and 2-methyl-1,3-propylene glycol. The method of synthesizing 2-methyl-1,3-propylene glycol monoglycidyl ether using an epihalohydrin as a halogenated alkylene oxide is explained below as an example. There are two methods of synthesis: (1) alkali metal dehalogenation with an alkali metal salt of a glycol and epihalohydrin, and (2) dehydrohalogenation reaction of a glycol and epihalohydrin.

2-Methyl-1,3-propylene glycol monoglycidyl ethers of this invention can be synthesized by either (1) or (2) of the methods of synthesis described above. A more specific example of the reaction described in (1) is presented here. To a solution of 2-methyl-1,3-propylene glycol in an aromatic hydrocarbon such as benzene, toluene, or xylene, a hydrocarbon such as hexane and cyclohexane, or an ether such as diethyl ether and tetrahydrofuran, metallic sodium, sodium hydride, metallic potassium, or potassium hydroxide was added. The mixture was stirred to ripen the salt, and epichlorohydrin was added dropwise at room temperature or at an elevated temperature. After the dropwise addition, the reaction was allowed to proceed for 5–7 hours with heating, and the sodium chloride or potassium chloride formed was removed by filtration. Next, the filtrate was distilled under reduced pressure to remove the solvent. After this, the residue was vacuum-distilled to obtain the desired clear and colorless 2-methyl-1,3-propylene glycol monoglycidyl ether.

As a standard method of synthesizing dialkylene oxide ethers, alkali metal dehalogenation with an alkali metal salt of the glycol and a halogenated alkylene oxide is used.

2-Methyl-1,3-propylene glycol dialkylene oxide ethers of this invention can also be prepared by the reaction mentioned above. The synthesis of 2-methyl-1,3-propylene glycol diglycidyl ether is described as a more specific example. 2-Methyl-1,3-propylene glycol is dissolved in an aromatic hydrocarbon solvent such as benzene, toluene, or xylene, or a hydrocarbon solvent such as hexane or cyclohexane, or an ether solvent such as diethyl ether or tetrahydrofuran. To this solution, an alkali metal such as metallic sodium, sodium hydride, metallic potassium or potassium hydroxide was added in either (1) 2 equivalents per equivalent of the glycol in one step, followed by dropwise addition of 2 equivalents of epichlorohydrin at room temperature or at an elevated temperature and heating for an addition 5–7 hours to complete the reaction, or (2) 1 equivalent added, followed by dropwise addition of 1 equivalent of epichlorohydrin at room temperature or at an elevated temperature and heating for an additional 5–7 hours to complete the reaction, followed by ripening of the salt by the addition of 1 equivalent and a second-stage reaction involving the addition of 1 equivalent of epichlorohydrin. After the completion of the reaction, sodium chloride or potassium chloride was filtered from the reaction mixture and the solvent was removed by distillation under reduced pressure. After this, the residue was distilled under vacuum to obtain the desired clear, colorless liquid substance which was 2-methyl-1,3-propylene glycol diglycidyl ether.

2-Methyl-1,3-propylene glycol mono- or di-alkylene oxide ethers of the invention contain a glycol component with a side-chain methyl group and have characteristics not yet observed in the mono- or di-glycidyl alkylene glycols of the prior art. For example, they have the polar effect derived from the electron-donating action of the methyl group, the releasing effect of the hydrogen atom (methine hydrogen atom) covalently bonded to the carbon atom with the methyl group, and a high reactivity of the terminal cross-linkable epoxy group and terminal hydroxyl group. Utilizing these characteristics, the compounds of this invention are expected to be used in a wide range of applications such as ultraviolet ray or heat cured paints, adhesives, nonwoven cloth binders, paper processing, modifying agent for copolymers, ion-exchange resins, dental material, and cross-linking agents, as starting materials, intermediates, and reactive diluents.

The invention will be explained below in respect to the photocurable composition.

The polyepoxy compounds of polyalcohols have a wide range of applications as curable compounds. For example, when they are used in photoresists, the said compound, a filler polymeric compound with a film-forming capability, a suitable sensitizer, dyes, and a thermal polymerization inhibitor are dissolved in an organic solvent to form a homogeneous solution, and the solution is applied to a base plate in a suitable thickness. The solvent is removed to form a film, and the film is exposed to an active ray to copy an image by a photographic method.

One of the possible applications of the 2-methyl-1,3-propylene glycol dialkylene oxide ether of this invention is in the curable composition used in the photoresist process. When the 2-methyl-1,3-propylene glycol dialkylene oxide ether was used in this application, the curing speed was surprisingly fast and an image whose adhesion to the base plate was excellent was obtained. Although the reason for this exceptional performance is not clearly understood at this point, the following explanation is advanced as a possible reason. 2-Methyl-1,3-propylene glycol, which is incorporated in the 2-methyl-1,3-propylene glycol dialkylene oxide ether, has a polar effect influenced by the electron-donating action of the methyl group bonded to the carbon atom in the 2 position and a releasing effect of the hydrogen atom (methine hydrogen atom) covalently bonded to the carbon atom, to which the methyl group is also bonded. These effects, in addition to the strong cross-linking effect of the terminal epoxy groups of the dialkylene oxide ether, are thought to contribute to the unusual properties of the compounds of this invention.

It is thought that the action of a cross-linking compound containing three functional groups is achieved by the two terminal epoxy groups which can be cross-linked by light. The amount of 2-methyl-1,3-propylene glycol alkylene oxide ether formulated in the curable composition of this invention should be preferably 20–80 wt.% or more preferably 30–60 wt.% without counting the amount of the solvent in the composition.

The filler polymeric compound formulated in the curable composition of this invention is represented by the polymeric compounds, such as the homopolymer or copolymer of acrylic acid or methacrylic acid, cellulose derivatives, polyvinyl alcohol, and polyacrylamide. Sensitizers such as Michler's ketone, N,N'-tetraethyl-4,4'-diaminobenzophenone, benzophenone, 5-nitroacenaphthene, 1,2-benzoanthraquinone, benzyl, benzoin, α-naphthoquinone, and 9-fluorenone can be used. Needless to say, 2-methyl-1,3-propylene glycol dialkylene oxide ether compounds of this invention can be mixed with other well-known polyfunctional unsaturated compounds such as pentaerythritol triacrylate and trimethylolpropane trimethacrylate in suitable proportions and still attain a comparable curing speed and produce images with excellent adhesion.

In the following paragraphs, this invention will be explained with examples, but it is not limited to these examples. In the examples, the term "part" signifies weight part. The infrared absorption spectra were taken on the Nippon Bunko IRA-2, and the nuclear magnetic resonance spectra were taken on the Nippon Denshi JNM-MH-100.

EXAMPLE 1

Ten parts of sodium hydride were dissolved in dry ether and 22 parts of 2-methyl-1,3-propylene glycol were added dropwise with agitation to the solution under a stream of nitrogen. After the completion of the dropwise addition, the reaction mixture was heated to reflux for two hours in order to complete the conversion to sodium salt. Next, 23 parts of epichlorohydrin were slowly added dropwise under reflux. After the completion of this dropwise addition, the refluxing was allowed to continue for three hours until sufficient progress of the reaction was confirmed. The sodium chloride formed was removed by filtration from the reaction mixture. The filtrate was dried with anhydrous magnesium sulfate and filtered. The solvent was removed under reduced pressure to yield 32 parts of a slightly yellow liquid. This liquid was distilled under vacuum to yield 28 parts of a clear, colorless liquid substance (73° C./0.5 mm Hg). The structure of the liquid substance obtained in this manner was established by elementary analysis, the infrared absorption spectrum, and nuclear magnetic resonance to be 2-methyl-1,3-propylene glycol monoglycidyl ether.

Elementary Analysis: Experimental—C 57.21, H 9.54; Calculated—C 57.51, H 9.65.

Infrared Absorption Spectrum:
3300–3450 cm$^{-1}$ alcoholic hydroxyl group
1020–1100 cm$^{-1}$ absorption derived from ether linkage
Nuclear Magnetic Resonance Spectrum:

| 3.4–3.8 ppm | methylene proton | 6H | |
| 3.45–3.8 ppm | hydroxyl group | 1H | (disappeared deuterium oxide exchange) |
| 3.05–3.20 ppm | epoxymethine proton | 1H | |
| 2.58–2.92 ppm | epoxymethylene proton | 2H | |
| 2.10 ppm | methine proton | 1H | |
| 0.95 ppm | methyl proton | 3H | |

EXAMPLE 2

Using dimethyl sulfoxide as a solvent, 23 parts of 2-methyl-1,3-propylene glycol and 40 parts of potassium hydroxide were vigorously agitated. The mixture was heated to 70° C. gradually over one hour, and 27 parts of epibromohydrin were added dropwise slowly over several hours. During this dropwise addition, the temperature of the reaction mixture was maintained at 70° C. The reaction mixture was maintained at 80° C. for two hours to complete the reaction. This reaction mixture was poured into ice water and the organic layer was separated. The separated organic layer was dried with anhydrous magnesium sulfate. The drying agent was separated by filtration and distilled under vacuum to yield 12 parts of colorless liquid substance (75° C./0.6 mm Hg). The structure of the liquid substance obtained in this manner was confirmed to be that of 2-methyl-1,3-propylene glycol monoglycidyl ether by elementary analysis, the infrared absorption spectrum, and the nuclear magnetic resonance spectrum.

Elementary Analysis: Experimental—C 57.73, H 9.70; Calculated—C 57.51, H 9.65.

Infrared Absorption Spectrum:
3300–3450 cm$^{-1}$ alcoholic hydroxyl group
1020–1100 cm$^{-1}$ absorption derived from ether linkage
Nuclear Magnetic Resonance Spectrum:

| 3.4–3.8 ppm | methylene proton | 6H | |
| 3.45–3.8 ppm | hydroxyl group | 1H | (disappeared deuterium oxide exchange) |
| 3.05–3.20 ppm | epoxy methine proton | 1H | |
| 2.58–2.92 ppm | epoxy methylene proton | 2H | |
| 2.10 ppm | methine proton | 1H | |
| 0.95 ppm | methyl proton | 3H | |

EXAMPLE 3

Ten parts of sodium hydride were dissolved in dry tetrahydrofuran as a solvent, and 22 parts of 2-methyl-1,3-propylene glycol were added dropwise to this solution with agitation under nitrogen. After the completion of the dropwise addition, the reaction mixture was heated to reflux for two hours in order to complete the conversion to the sodium salt. Next, 23 parts of epichlorohydrin were slowly added dropwise while the reaction mixture was refluxed. After the completion of this dropwise addition, the refluxing was continued for three hours to insure that the reaction progressed sufficiently. The reaction mixture was cooled to room temperature and an additional ten parts of sodium hydride were added. The procedure described above was repeated and 23 parts of epichlorohydrin were added. The reaction mixture was refluxed for five hours. Next, sodium chloride was filtered from the reaction mixture, and the filtrate was dried with anhydrous magnesium sulfate. The anhydrous magnesium sulfate was filtered, and the solvent was removed under reduced pressure to yield 40 parts of slightly yellow liquid substance. This substance was distilled under vacuum to yield 32 parts of clear, colorless liquid substance (132° C./0.8 mm Hg). The liquid substance obtained in this manner was examined by elementary analysis, infrared absorption, and nuclear magnetic resonance. The structure of this substance was confirmed to be that of 2-methyl-1,3-propylene glycol diglycidyl ether.

Elementary Analysis: Experimental—C 59.69, H 8.71; Calculated—C 59.39, H 8.97.

Infrared Absorption Spectrum:
1060–1140 cm$^{-1}$ absorption derived from ether linkage
Nuclear Magnetic Resonance Spectrum:

| 3.40–3.85 ppm | methylene proton | 8H |
| 3.05–3.25 ppm | epoxymethine proton | 2H |
| 2.50–2.92 ppm | epoxy methylene proton | 4H |
| 2.05 ppm | methine proton | 1H |
| 0.95 ppm | methyl proton | 3H |

EXAMPLE 4

Twenty-one parts of sodium hydride were dissolved in dry tetrahydrofuran as a solvent, and 21 parts of 2-methyl-1,3-propylene glycol were added dropwise with agitation under nitrogen. After the completion of the dropwise addition, the reaction mixture was refluxed for three hours to complete the formation of the sodium salt. The reaction mixture continued to be refluxed, and 45 parts of epichlorohydrin were slowly added dropwise. After the completion of the dropwise addition, the reaction mixture continued to be refluxed for 5–7 hours to make certain that the reaction progressed sufficiently. The reaction mixture was treated in the manner described in Example 3 to yield 40 parts of clear, colorless liquid substance (130° C./0.8 mm Hg). The structure of the liquid substance obtained in this manner was established by elementary analysis, infrared absorption, and nuclear magnetic resonance to be that of 2-methyl-1,3-propylene glycol diglycidyl ether.

Elementary Analysis: Experimental—C 59.14, H 9.10; Calculated—C 59.39, H 8.97.

The infrared absorption spectrum and nuclear magnetic resonance spectrum of the product obtained in this example were identical to the ones obtained for the product of Example 1, namely, 2-methyl-1,3-propylene glycol diglycidyl ether.

EXAMPLE 5

| compound obtained in Example 3 | 10 parts |
| polymethacrylic acid (average molecular weight about 60,000) | 12.5 |
| Michler's ketone | 1.0 part |
| crystal violet | 0.05 |
| hydroquinone | 0.05 |

| | |
|---|---|
| toluene | 50 |

The composition described above was vigorously agitated for about 10 minutes with a homogenizer to finely disperse the pigment. The liquid composition obtained in this manner was applied on a PET film (75 μm) using a Meabar coater. The applied liquid was dried for 5 minutes at 60° C. to yield a blue sheet whose thickness was ca. 5 μm. Next, the light-sensitive film obtained in this manner was sealed to a photographic clear negative and exposed for about 120 seconds at 40 cm distance from the light source in an Orc jet printer (Orc Seisakusho, 2 kW mercury lamp). After the exposure to light, the exposed parts turned yellow immediately and the latent image was recognizable. The film was treated for 5 minutes at 100° C. immediately and developed in a mixture of 10 parts toluene and 90 parts n-hexane. The compound in the unexposed section was removed from the PET film; the light-cured section was insoluble and remained on the PET film. The adhesion of the resist obtained in this manner on the PET base plate was excellent.

EXAMPLE 6

| | |
|---|---|
| compound obtained in Example 4 | 10 parts |
| polyacrylic acid (average molecular weight about 70,000) | 12.5 |
| benzophenone | 0.8 |
| crystal violet | 0.05 |
| hydroquinone | 0.2 |
| tetrachloroethane | 50 |

The composition described above was treated in the manner described in Example 5 to disperse the pigment and was applied on a PET film. The applied film was dried; the thickness of the dried film was ca. 5 μm. The film was exposed to light in the manner described in Example 5 and the latent image developed yellow. Immediately, the film was heated for 5 minutes at 100° C. and developed in a mixture of 10 parts tetrachloroethane, 10 parts toluene, and 80 parts n-hexane. A very good image was obtained. The resist obtained in this manner adhered excellently to the PET base plate as in Example 5.

COMPARISON EXAMPLE 1

| | |
|---|---|
| diethylene glycol diacrylate | 10 parts |
| polymethacrylic acid (average molecular weight 60,000) | 12.5 |
| Michler's ketone | 1.0 |
| crystal violet | 0.05 |
| hydroquinone | 0.05 |
| toluene | 50 |

The composition described above was treated in the manner described in Example 5 to disperse the pigment and was applied on a PET film. The applied film was dried; the thickness of the dried film was ca. 5 μm. The film was exposed to light in the manner described in Example 5, and the latent image was recognizable. Next, the exposed film was developed with the development mixture described in Example 5 (10 parts toluene and 90 parts n-hexane) to obtain an image, but a portion of the image peeled from the PET film during the developing procedure.

What is claimed is:

1. 2-Methyl-1,3-propylene glycol mono- or di-alkylene oxide ether having the formulae (I) or (II):

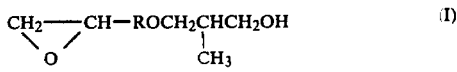

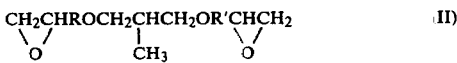

in which R and R' are linear or branched alkylene groups with $C_1-C_3$.

2. A curable composition which contains as an effective ingredient 2-methyl-1,3-propylene glycol di-alkylene oxide ether as defined in claim 1.

* * * * *